United States Patent
Sharma et al.

(10) Patent No.: US 9,561,242 B2
(45) Date of Patent: *Feb. 7, 2017

(54) DOXYCYCLINE COMPOSITION

(71) Applicant: SUN PHARMACEUTICAL INDUSTRIES LIMITED, Mumbai, Maharashtra (IN)

(72) Inventors: Ravish Kumar Sharma, Khargone (IN); Pulak Kumar Metia, Howrah (IN); Ravinder Singh, Gurgaon (IN); Rajesh Srikrishan Shear, Gurgaon (IN); Anuj Kumar Fanda, Ghaziabad (IN); Satish Kumar Jain, Bilaspur (IN); Romi Barat Singh, Varanasi (IN); Swarna Pappu, Monroe, NJ (US); Prabhakar Konatham, Monmouth Junction, NJ (US); Pruthvipathy Katikaneni, Parsippany, NJ (US); Dileep Jami, Srikakulam (IN)

(73) Assignee: Sun Pharmaceutical Industries Limited, Mumbai (IN)

(*) Notice: Subject to any disclaimer, the term of this patent is extended or adjusted under 35 U.S.C. 154(b) by 0 days.

This patent is subject to a terminal disclaimer.

(21) Appl. No.: 15/013,122

(22) Filed: Feb. 2, 2016

(65) Prior Publication Data
US 2016/0151397 A1    Jun. 2, 2016

Related U.S. Application Data

(63) Continuation-in-part of application No. 14/821,263, filed on Aug. 7, 2015, which is a continuation-in-part of application No. 14/326,949, filed on Jul. 9, 2014, now Pat. No. 9,132,092, application No. 15/013,122, which is a continuation of application No. 14/821,280, filed on Aug. 7, 2015, which is a continuation-in-part of application No. 14/548,915, filed on Nov. 20, 2014.

(30) Foreign Application Priority Data

Mar. 23, 2015  (IN) .............................. 791/DEL/2015

(51) Int. Cl.
*A61K 31/65* (2006.01)
*A61K 9/20* (2006.01)
*A61K 9/24* (2006.01)

(52) U.S. Cl.
CPC ............... *A61K 31/65* (2013.01); *A61K 9/209* (2013.01); *A61K 9/2027* (2013.01); *A61K 9/2054* (2013.01); *A61K 9/2081* (2013.01)

(58) Field of Classification Search
CPC .................................................... A61K 9/209
USPC .......................................... 514/152; 424/465
See application file for complete search history.

(56) References Cited

U.S. PATENT DOCUMENTS

| | | | |
|---|---|---|---|
| 7,749,532 B2 | 7/2010 | Chang et al. | 424/458 |
| 8,652,516 B1 | 2/2014 | Etchegaray et al. | 424/452 |
| 9,132,092 B1* | 9/2015 | Sharma | A61K 9/2054 |

OTHER PUBLICATIONS

Agwuh et al., "Pharmacokinetics and pharmacodynamics of the tetracyclines including glycylcyclines," *Journal of Antimicrobial Chemotherapy*, 58(2):256-265 (2006).

* cited by examiner

*Primary Examiner* — Raymond Henley, III

(57) ABSTRACT

The present invention relates to a once daily pharmaceutical composition comprising doxycycline, a controlled-release polymer, and one or more pharmaceutically acceptable excipients. The invention further provides a method of treatment of rosacea by administering such pharmaceutical composition. A process of preparing such pharmaceutical composition is also provided.

14 Claims, No Drawings

DOXYCYCLINE COMPOSITION

This application is a continuation-in-part of U.S. application Ser. No. 14/821,263, filed on Aug. 7, 2015 (pending). U.S. application Ser. No. 14/821,263 is a continuation-in-part of U.S. application Ser. No. 14/326,949, filed on Jul. 9, 2014 (now U.S. Pat. No. 9,132,092). This application is a continuation of U.S. application Ser. No. 14/821,280, filed on Aug. 7, 2015 (pending). U.S. application Ser. No. 14/821,280 is a continuation-in-part of U.S. application Ser. No. 14/548,915, filed on Nov. 20, 2014 (pending).

FIELD OF THE INVENTION

The present invention relates to a once daily pharmaceutical composition comprising doxycycline, a controlled-release polymer, and one or more pharmaceutically acceptable excipients. The invention further provides a method of treatment of rosacea by administering such pharmaceutical composition. A process of preparing such pharmaceutical composition is also provided.

BACKGROUND OF THE INVENTION

Food effect refers to food-drug interactions which lead to either a decrease or an increase of the extent of drug absorption. The commercially available capsules of doxycycline (Oracea® 40 mg capsules) for the treatment of inflammatory lesions (papules and pustules) of rosacea is a combination of immediate-release (30 mg) and delayed-release (10 mg) components. As per the prescribing information, Oracea has significant food effect and thus is recommended to be taken on an empty stomach, preferably at least one hour prior to or two hours after meals. Its $C_{max}$ and $AUC_{0-t}$ decrease by 45% and 22%, respectively, when taken along with food.

Therefore, there exists a need for a pharmaceutical composition of doxycycline which is capable of reducing the food effect of doxycycline. The present inventors have developed a pharmaceutical composition of doxycycline with reduced food effect which would enable the patient to take the drug without regard to meals, thereby improving patient convenience and compliance.

SUMMARY OF THE INVENTION

The present invention relates to a once daily pharmaceutical composition comprising doxycycline, a controlled-release polymer and one or more pharmaceutically acceptable excipients. The invention further provides a method of treatment of rosacea by administering such pharmaceutical composition. A process of preparing such pharmaceutical composition is also provided. It is possible to reduce the dose if food effect is minimized, as the same therapeutic levels may be achieved with a lesser amount of doxycycline.

DETAILED DESCRIPTION OF THE INVENTION

A first aspect of the invention provides a once daily pharmaceutical composition comprising doxycycline, a controlled-release polymer, and one or more pharmaceutically acceptable excipients, wherein the pharmaceutical composition contains up to 40 mg of doxycycline.

According to one embodiment of the above aspect, the pharmaceutical composition contains from 24 mg to 40 mg of doxycycline.

According to another embodiment of the above aspect, the pharmaceutical composition contains 40 mg of doxycycline.

According to another embodiment of the above aspect, the pharmaceutical composition contains 36 mg of doxycycline.

According to another embodiment of the above aspect, the pharmaceutical composition contains 32 mg of doxycycline.

According to another embodiment of the above aspect, the pharmaceutical composition contains 30 mg of doxycycline.

According to yet another embodiment of the above aspect, the pharmaceutical composition is a capsule or a tablet.

A second aspect of the invention provides a once daily pharmaceutical composition comprising doxycycline and one or more pharmaceutically acceptable excipients, wherein the pharmaceutical composition exhibits a reduced food effect such that the food effect on $C_{max}$ is less than 40% and/or $AUC_{0-t}$ is less than 20% as compared to when the pharmaceutical composition is administered in a fasted state.

According to one embodiment of the above aspect, the food effect on $C_{max}$ is less than 20% as compared to when the pharmaceutical composition is administered in a fasted state.

According to another embodiment of the above aspect, the once daily pharmaceutical composition comprises (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion.

According to the above embodiment, the immediate-release portion contains 85% of doxycycline and the controlled-release portion contains 15% of doxycycline.

According to the above embodiment, the immediate-release portion contains 34 mg of doxycycline and the controlled-release portion contains 6 mg of doxycycline.

According to the above embodiment, the immediate-release portion contains 75% of doxycycline and the controlled-release portion contains 25% of doxycycline.

According to the above embodiment, the immediate-release portion contains 30 mg of doxycycline and the controlled-release portion contains 10 mg of doxycycline.

According to the above embodiment, the immediate-release portion contains 66% of doxycycline and the controlled-release portion contains 34% of doxycycline.

According to the above embodiment, the immediate-release portion contains 26.4 mg of doxycycline and the controlled-release portion contains 13.6 mg of doxycycline.

According to the above embodiment, the immediate-release portion contains 65% of doxycycline and the controlled-release portion contains 35% of doxycycline.

According to the above embodiment, the immediate-release portion contains 26 mg of doxycycline and the controlled-release portion contains 14 mg of doxycycline.

According to the above embodiment, the immediate-release portion contains 60% of doxycycline and the controlled-release portion contains 40% of doxycycline.

According to the above embodiment, the immediate-release portion contains 24 mg of doxycycline and the controlled-release portion contains 16 mg of doxycycline.

According to another embodiment of the above aspect, the pharmaceutical composition comprises only the immediate-release portion.

According to another embodiment of the above aspect, the pharmaceutical composition comprises only the controlled-release portion.

A third aspect of the present invention provides a process for the preparation of a once daily pharmaceutical composition comprising doxycycline and one or more pharmaceutically acceptable excipients, wherein the pharmaceutical composition exhibits a reduced food effect, and wherein the process comprises:
  a) preparing an immediate-release portion comprising doxycycline and one or more pharmaceutically acceptable excipients;
  b) preparing a controlled-release portion comprising doxycycline, a controlled-release polymer, and one or more pharmaceutically acceptable excipients; and
  c) formulating the immediate-release portion and the controlled-release portion into a pharmaceutical composition.

According to one embodiment of the above aspect, the pharmaceutical composition is a capsule or a tablet.

According to another embodiment of the above aspect, the pharmaceutical composition comprises only the immediate-release portion.

According to another embodiment of the above aspect, the pharmaceutical composition comprises only the controlled-release portion.

A fourth aspect of the present invention provides a method of treating rosacea by administering to a person in need thereof a once daily pharmaceutical composition comprising doxycycline and one or more pharmaceutically acceptable excipients, wherein the pharmaceutical composition exhibits a reduced food effect such that the food effect on $C_{max}$ is less than 40% and/or $AUC_{0-t}$ is less than 20% as compared to when the pharmaceutical composition is administered in a fasted state.

A fifth aspect of the present invention provides a method of treating rosacea by administering to a person in need thereof a once daily pharmaceutical composition comprising doxycycline, a controlled-release polymer, and one or more pharmaceutically acceptable excipients, wherein the pharmaceutical composition contains up to 40 mg of doxycycline.

The term "doxycycline," as used herein, includes doxycycline base and its pharmaceutically acceptable salts, hydrates, solvates, esters, or prodrugs. The preferred forms are the monohydrate form and the hyclate form.

The term "bioavailability," as used herein, refers to the fraction of a drug that reaches systemic circulation after oral administration. Parameters used in the measurement of bioavailability are $C_{max}$ (maximum plasma concentration), $AUC_{0-t}$ (area under the curve), and $T_{max}$ (time to reach maximum plasma concentration), which are well known in the art.

The term "food effect," as used herein, refers to the relative difference in $AUC_{0-t}$ and $C_{max}$ of a drug when it is administered in a fed state as compared to when it is administered in a fasted state.

The term "reduced food effect," as used herein, refers to a state wherein food decreases $C_{max}$ and $AUC_{0-t}$ by less than 40% and 20%, respectively, in a fed state when compared to $C_{max}$ and $AUC_{0-t}$ in a fasted state.

The term "fasted state," as used herein, refers to a gap of at least two hours between the meal and administration of the pharmaceutical composition.

The term "fed state," as used herein, refers to administration from about 1 hour before a meal to about 1 hour after a meal.

The term "immediate-release portion," as used herein, refers to that portion of the pharmaceutical composition which releases the drug immediately upon contact with gastric juices.

The term "controlled-release portion," as used herein, refers to that portion of the pharmaceutical composition which contains a controlled-release polymer and releases the drug in a controlled manner over a period of time. Controlled-release can also be referred to as sustained release (SR), prolonged release (PR), or extended release (ER).

Suitable controlled-release polymers are selected from the group comprising hydroxypropylmethyl cellulose, hydroxypropyl cellulose, methyl cellulose, sodiumcarboxymethyl cellulose, hydroxyethyl cellulose, carboxymethyl ethyl cellulose, ethyl cellulose, cellulose acetate, cellulose nitrate, polymethacrylic copolymer, poloxamers, polyoxyethylene stearate, polyvinyl pyrrolidone, polyvinyl pyrrolidone-polyvinylacetate copolymer, polyvinyl alcohol, polyethylene oxide, gums (e.g., xanthan gum, tragacanth gum, gum karaya, guar gum, acacia gum, and locust bean gum), fatty acids, fatty acid esters, alkyl alcohols, wax, shellac, and mixtures thereof.

The term "pharmaceutically acceptable excipients," as used herein, includes any physiologically inert additives that are routinely used in pharmaceutical compositions. Pharmaceutically acceptable excipients are selected from the group comprising binders, diluents, disintegrants, lubricants/glidants/antiadherants, acidifying agents, and mixtures thereof.

Examples of binders include povidone, copovidone, polyvinyl pyrrolidone, hydroxypropylmethyl cellulose, hydroxypropyl cellulose, hydroxyethyl cellulose, methyl cellulose, ethyl cellulose, xanthan gum, gum acacia, gum arabic, tragacanth, sorbitol, dextrose, sucrose, mannitol, gelatin, pullulan, sodium alginate, calcium alginate, ammonium calcium alginate, propylene glycol, polyvinyl alcohol, corn syrup, methacrylates, carboxyvinyl polymers, e.g., carbomers, and mixtures thereof.

Examples of diluents include microcrystalline cellulose, powdered cellulose, dibasic calcium phosphate, tribasic calcium phosphate, calcium sulfate, calcium carbonate, lactose monohydrate, lactose anhydrous, sucrose, sorbitol, xylitol, erythritol, kaolin, calcium silicate, maltodextrin, starch, modified starch (e.g., pregelatinized starch, maize starch, and corn starch), and mixtures thereof.

Examples of disintegrants include hydroxypropyl cellulose (L-HPC), crospovidone, croscarmellose sodium, carboxymethyl cellulose sodium, carboxymethyl cellulose calcium, sodium starch glycolate, gums, alginic acid or alginates, starch, corn starch, modified starch, carboxymethyl starch, polyacrylates, and mixtures thereof.

Examples of lubricants/glidants/antiadherents include magnesium stearate, hydrogenated vegetable oil, glyceryl behenate, glyceryl monostearate, stearic acid, sodium stearyl fumarate, calcium stearate, zinc stearate, aluminum silicate, talc, colloidal silicon dioxide, sucrose esters of fatty acids, waxes, silica gel, and mixtures thereof.

Acidifying agents are pH modifiers which provide an acidic environment required for stability of the drug. Examples of acidifying agents include citric acid, tartaric acid, adipic acid, fumaric acid, malic acid, acetic acid, lactic acid, hydrochloric acid, phosphoric acid, and mixtures thereof.

Various solvents that may be employed during the preparation of the pharmaceutical composition of the present invention are selected from the group comprising methyl alcohol, ethyl alcohol, isopropyl alcohol, n-butyl alcohol, acetone, acetonitrile, chloroform, methylene chloride, water, and mixtures thereof.

The pharmaceutical composition of the present invention may be prepared by any of the well-known processes including wet granulation, dry granulation, direct compression, top spray granulation, and drug layering. The immediate-release portion and the controlled-release portion may be in the form of pellets, beads, beadlets, granules, spheres or spheroids, minitablets, particles, or powders.

The pharmaceutical composition may be further coated with a film coating prepared by using a film-forming polymer and one or more pharmaceutically acceptable excipients. The pharmaceutically acceptable excipients may be plasticizers, opacifiers, coloring agents, and mixtures thereof.

Examples of film-forming polymers include hydroxypropylmethyl cellulose, ethyl cellulose, methyl cellulose, hydroxyethyl cellulose, hydroxypropyl cellulose, sodium carboxymethyl cellulose, cellulose acetate, hydroxypropylmethyl cellulose phthalate, cellulose acetate trimellitate, methacrylic acid copolymers (e.g., Eudragit®), polyvinyl pyrrolidone, polyvinyl alcohol, polyethylene glycol, and mixtures thereof. A preferred film-forming polymer is hydroxypropylmethyl cellulose. Other suitable film-forming polymers which are known in the art may also be used. Alternatively, commercially available coating for pharmaceutical compositions comprising film-forming polymers marketed under various trade names, such as Opadry® and Opaglos®, may also be used.

Examples of plasticizers include propylene glycol, triethyl citrate, tributyl citrate, dibutyl sebacate, acetyl tributyl citrate, glyceryl monostearate, triacetin, polyethylene glycol, diethyl phthalate, acetylated monoglycerides, diacetylated monoglycerides, cetyl alcohol, and mixtures thereof.

Examples of opacifiers include titanium dioxide, manganese dioxide, iron oxide, silicon dioxide, and mixtures thereof.

The coloring agents may be selected from FDA approved colorants such as iron oxide, lake of tartrazine, allura red, titanium dioxide, and mixtures thereof.

The coating may be carried out by using any conventional coating techniques known in the art, such as spray coating in a conventional coating pan or fluidized bed processor, or dip coating.

The following examples illustrate the present invention but are not to be construed as limiting the scope of the invention.

EXAMPLES

Example 1

| Ingredients | Quantity (% w/w) |
|---|---|
| Immediate-Release Layer | |
| Doxycycline hyclate equivalent to doxycycline base 24 mg | 9.60 |
| Microcrystalline cellulose (Avicel ® PH-102) | 33.50 |
| Crospovidone | 2.91 |
| Polyvinyl pyrrolidone | 1.70 |
| Colloidal silicon dioxide | 0.24 |
| Iron oxide yellow | 0.49 |
| Magnesium stearate | 0.10 |
| Controlled-Release Layer | |
| Doxycycline hyclate equivalent to doxycycline base 16 mg | 6.40 |
| Microcrystalline cellulose (Avicel ® PH-102) | 16.38 |
| Microcrystalline cellulose (Avicel ® PH-200) | 13.88 |
| Hydroxypropylmethyl cellulose (Methocel ® K4M Premium CR) | 4.85 |
| Hydroxypropylmethyl cellulose (Methocel ® K100 Premium LV) | 4.85 |
| Polyvinyl pyrrolidone | 1.46 |
| Colloidal silicon dioxide | 0.24 |
| Magnesium stearate | 0.49 |
| Coating | |
| Opadry ® | 2.91 |
| Purified water | q.s. |

Manufacturing Process

Immediate-Release Portion

1. Doxycycline hyclate, Avicel® PH-102, iron oxide yellow, crospovidone, polyvinyl pyrrolidone, colloidal silicon dioxide, and magnesium stearate were mixed to form a blend.

Controlled-Release Portion

2. Doxycycline hyclate, Avicel® PH-102, Avicel® PH-200, Methocel® K4M, Methocel® K100, polyvinyl pyrrolidone, and colloidal silicon dioxide were mixed to form a blend.

3. The blend obtained in step 2 was lubricated with magnesium stearate to form a final blend.

Compression

4. The blend obtained in step 1 was compressed, followed by compression of the final blend obtained in step 3 to form bilayer tablets.

5. Opadry® was dispersed in purified water to form a dispersion.

6. The tablets of step 4 were coated with the Opadry® dispersion of step 5.

Example 2

| Ingredients | Quantity (% w/w) |
|---|---|
| Immediate-Release Layer | |
| Doxycycline hyclate equivalent to doxycycline base 26.4 mg | 10.56 |
| Microcrystalline cellulose (Avicel ® PH-102) | 32.54 |
| Crospovidone | 2.91 |
| Polyvinyl pyrrolidone | 1.70 |
| Colloidal silicon dioxide | 0.24 |
| Iron oxide yellow | 0.49 |
| Magnesium stearate | 0.10 |
| Controlled-Release Layer | |
| Doxycycline hyclate equivalent to doxycycline base 13.6 mg | 5.44 |
| Microcrystalline cellulose (Avicel ® PH-102) | 17.34 |
| Microcrystalline cellulose (Avicel ® PH-200) | 13.87 |
| Hydroxypropylmethyl cellulose (Methocel ® K4M Premium CR) | 2.43 |
| Hydroxypropylmethyl cellulose (Methocel ® K100 Premium LV) | 7.28 |
| Polyvinyl pyrrolidone | 1.46 |
| Colloidal silicon dioxide | 0.24 |
| Magnesium stearate | 0.49 |

| Ingredients | Quantity (% w/w) |
|---|---|
| Coating | |
| Opadry® | 2.91 |
| Purified water | q.s. |

Manufacturing Process
Immediate-Release Portion
1. Doxycycline hyclate, Avicel® PH-102, iron oxide yellow, crospovidone, polyvinyl pyrrolidone, colloidal silicon dioxide, and magnesium stearate were mixed to form a blend.

Controlled-Release Portion
2. Doxycycline hyclate, Avicel® PH-102, Avicel® PH-200, Methocel® K4M, Methocel® K100, polyvinyl pyrrolidone, and colloidal silicon dioxide were mixed to form a blend.
3. The blend obtained in step 2 was lubricated with magnesium stearate to form a final blend.

Compression
4. The blend obtained in step 1 was compressed, followed by compression of the final blend obtained in step 3 to form bilayer tablets.
5. Opadry® was dispersed in purified water to form a dispersion.
6. The tablets of step 4 were coated with the Opadry® dispersion of step 5.

Example 3

| Ingredients | Quantity (% w/w) |
|---|---|
| Immediate-Release Layer | |
| Doxycycline hyclate equivalent to doxycycline base 34 mg | 13.61 |
| Microcrystalline cellulose (Avicel® PH-102) | 29.50 |
| Crospovidone | 2.91 |
| Polyvinyl pyrrolidone | 1.70 |
| Colloidal silicon dioxide | 0.24 |
| Iron oxide yellow | 0.49 |
| Magnesium Stearate | 0.10 |
| Controlled-Release Layer | |
| Doxycycline hyclate equivalent to doxycycline base 6 mg | 2.40 |
| Microcrystalline cellulose (Avicel® PH-102) | 17.95 |
| Microcrystalline cellulose (Avicel® PH-200) | 13.87 |
| Hydroxypropylmethyl cellulose (Methocel® K100 Premium LV) | 12.14 |
| Polyvinyl pyrrolidone | 1.46 |
| Colloidal silicon dioxide | 0.24 |
| Magnesium stearate | 0.48 |
| Coating | |
| Opadry® | 2.91 |
| Purified water | q.s. |

Manufacturing Process
Immediate-Release Portion
1. Doxycycline hyclate, Avicel® PH-102, iron oxide yellow, crospovidone, polyvinyl pyrrolidone, colloidal silicon dioxide, and magnesium stearate were mixed to form a blend.

Controlled-Release Portion
2. Doxycycline hyclate, Avicel® PH-102, Avicel® PH-200, Methocel® K100, polyvinyl pyrrolidone, and colloidal silicon dioxide were mixed to form a blend.
3. The blend obtained in step 2 was lubricated with magnesium stearate to form a final blend.

Compression
4. The blend obtained in step 1 was compressed, followed by compression of the final blend obtained in step 3 to form bilayer tablets.
5. Opadry® was dispersed in purified water to form a dispersion.
6. The tablets of step 4 were coated with the Opadry® dispersion of step 5.

Example 4

| Ingredients | Quantity (% w/w) |
|---|---|
| Immediate-Release Portion | |
| Doxycycline hyclate equivalent to doxycycline base 30 mg | 11.20 |
| Microcrystalline cellulose | 32.49 |
| Crospovidone | 2.43 |
| Polyvinyl pyrrolidone | 1.70 |
| Magnesium stearate | 0.49 |
| Colloidal silicon dioxide | 0.24 |
| Controlled-Release Portion | |
| Doxycycline hyclate equivalent to doxycycline base 10 mg | 3.73 |
| Microcrystalline cellulose | 29.76 |
| Hydroxypropylmethyl cellulose (Methocel® K100 LVCR) | 7.28 |
| Hydroxypropylmethyl cellulose (Methocel® K4M CR) | 7.28 |
| Magnesium stearate | 0.49 |
| Film Coating | |
| Opadry® | 2.91 |
| Purified water | q.s. |

Manufacturing Process
Immediate-Release Portion
1. Doxycycline hyclate, microcrystalline cellulose, crospovidone, and polyvinyl pyrrolidone are blended.
2. The blend obtained in step 1 is mixed with magnesium stearate and colloidal silicon dioxide to obtain a final blend.

Controlled-Release Portion
3. Doxycycline hyclate, microcrystalline cellulose, and hydroxypropylmethyl cellulose polymers are blended.
4. Magnesium stearate is added to the blend of step 3 to obtain a final blend.

Compression
5. The blends obtained in step 2 and step 4 are compressed to form a bilayer tablet.
6. The bilayer tablet obtained in step 5 is film-coated using an Opadry® solution.

Example 5

| Ingredients | Quantity (% w/w) |
|---|---|
| Immediate-Release Portion | |
| Doxycycline hyclate equivalent to doxycycline base 30 mg | 11.20 |
| Microcrystalline cellulose | 32.49 |
| Crospovidone | 2.43 |
| Polyvinyl pyrrolidone | 1.70 |
| Magnesium stearate | 0.49 |
| Colloidal silicon dioxide | 0.24 |

-continued

| Ingredients | Quantity (% w/w) |
| --- | --- |
| Controlled-Release Portion | |
| Doxycycline hyclate equivalent to doxycycline base 10 mg | 3.73 |
| Polyvinyl pyrrolidone | 1.46 |
| Microcrystalline cellulose | 28.31 |
| Hydroxypropylmethyl cellulose (Methocel ® K100 LVCR) | 7.28 |
| Hydroxypropylmethyl cellulose (Methocel ® K4M CR) | 7.28 |
| Purified water | q.s. |
| Magnesium stearate | 0.48 |
| Film Coating | |
| Opadry ® | 2.91 |
| Purified water | q.s. |

Manufacturing Process
Immediate-Release Portion
1. Doxycycline hyclate, microcrystalline cellulose, crospovidone, and polyvinyl pyrrolidone are blended.
2. The blend obtained in step 1 is mixed with magnesium stearate and colloidal silicon dioxide to obtain a final blend.

Controlled-Release Portion
3. Polyvinyl pyrrolidone is dissolved in purified water to form a binder solution.
4. Doxycycline hyclate is added to the binder solution obtained in step 3 to form a drug-binder solution.
5. Microcrystalline cellulose and hydroxypropylmethyl cellulose are loaded into a top spray granulation assembly and are granulated using the drug-binder solution of step 4 to obtain granules.
6. The granules obtained in step 5 are lubricated with magnesium stearate.

Compression
7. The blend obtained in step 2 and the lubricated granules obtained in step 6 are compressed to form a bilayer tablet.
8. The bilayer tablet obtained in step 7 is film-coated using an Opadry® solution.

Example 6

| Ingredients | Quantity (% w/w) |
| --- | --- |
| Drug Layering | |
| Non pareil seeds | 26.25 |
| Doxycycline hyclate equivalent to doxycycline base 10 mg | 3.03 |
| Hydroxypropylmethyl cellulose | 0.63 |
| Purified water | q.s. |
| Controlled-Release Portion | |
| Ethyl cellulose | 3.56 |
| Dibutyl sebacate | 0.37 |
| Hydroxypropylmethyl cellulose | 0.19 |
| Isopropyl alcohol | q.s. |
| Purified water | q.s. |
| Colloidal silicon dioxide | 0.37 |
| Immediate-Release Portion | |
| Doxycycline hyclate equivalent to doxycycline base 30 mg | 9.38 |
| Microcrystalline cellulose | 53.00 |
| Crospovidone | 1.97 |
| Polyvinyl pyrrolidone | 0.66 |
| Magnesium stearate | 0.39 |
| Colloidal silicon dioxide | 0.20 |

Manufacturing Process
Drug Layering
1. Hydroxypropylmethyl cellulose is dissolved in purified water to form a binder solution.
2. Doxycycline hyclate is added to the binder solution of step 1 to form a drug-binder solution.
3. Sugar spheres are coated using the drug-binder solution obtained in step 2 to obtain drug-layered sugar spheres.
4. The drug-layered sugar spheres obtained in step 3 are dried.

Controlled-Release Portion
5. Isopropyl alcohol and purified water are mixed, and then dibutyl sebacate is added to the mixture, followed by the addition of ethyl cellulose and hydroxypropylmethyl cellulose with continuous stirring to form a clear solution.
6. Colloidal silicon dioxide is dispersed in the clear solution obtained in step 5 to form a coating solution.
7. The drug-layered dried sugar spheres obtained in step 4 are coated with the coating solution obtained in step 6 to obtain coated pellets.

Immediate-Release Portion
8. Doxycycline hyclate, microcrystalline cellulose, crospovidone, and polyvinyl pyrrolidone are blended.
9. The blend obtained in step 8 is mixed with magnesium stearate and colloidal silicon dioxide to obtain a final blend.

Compression
10. The coated pellets obtained in step 7 and the final blend obtained in step 9 are compressed to form a tablet.

Example 7

| Ingredients | Quantity (% w/w) |
| --- | --- |
| Drug Layering | |
| Non pareil seeds | 28.74 |
| Doxycycline hyclate equivalent to doxycycline base 10 mg | 3.32 |
| Hydroxypropylmethyl cellulose | 0.68 |
| Purified water | q.s. |
| Controlled-Release Portion | |
| Ethyl cellulose | 3.90 |
| Dibutyl sebacate | 0.41 |
| Hydroxypropylmethyl cellulose | 0.21 |
| Isopropyl alcohol | q.s. |
| Purified water | q.s. |
| Colloidal silicon dioxide | 0.41 |
| Immediate-Release Portion | |
| Doxycycline hyclate equivalent to doxycycline base 30 mg | 10.27 |
| Hydroxypropylmethyl cellulose | 2.05 |
| Purified water | q.s. |
| Compression Blend | |
| Microcrystalline cellulose | 43.11 |
| Crospovidone | 4.31 |
| Hydroxypropyl cellulose | 2.01 |
| Magnesium stearate | 0.58 |

Manufacturing Process
Drug Layering
1. Hydroxypropylmethyl cellulose is dissolved in purified water to form a binder solution.
2. Doxycycline hyclate is added to the binder solution of step 1 to form a drug-binder solution.
3. Sugar spheres are coated using the drug-binder solution of step 2 to obtain drug-layered sugar spheres.
4. The drug-layered sugar spheres obtained in step 3 are dried.

Controlled-Release Portion
5. Isopropyl alcohol and purified water are mixed, and then dibutyl sebacate is added to the mixture, followed by the addition of ethyl cellulose and hydroxypropylmethyl cellulose under continuous stirring to form a clear solution.
6. Colloidal silicon dioxide is then dispersed in the clear solution obtained in step 5 to form a coating solution.
7. The drug-layered dried sugar spheres obtained in step 4 are coated with the coating solution obtained in step 6 to obtain coated pellets.

Immediate-Release Portion
8. Hydroxypropylmethyl cellulose is dissolved in purified water, and doxycycline hyclate is added to obtain a drug-binder solution.
9. The drug-binder solution obtained in step 8 is coated onto the coated pellets obtained in step 7.

Compression
10. Microcrystalline cellulose, crospovidone, and hydroxypropyl cellulose are blended.
11. The blend obtained in step 10 is lubricated with magnesium stearate.
12. The coated pellets obtained in step 9 and the lubricated blend obtained in step 11 are compressed to form a tablet.

Example 8

| Ingredients | Quantity (% w/w) |
|---|---|
| Immediate-Release Portion | |
| Doxycycline hyclate equivalent to doxycycline base 30 mg | 11.99 |
| Microcrystalline cellulose (Avicel ® PH-102) | 31.07 |
| Crospovidone | 2.91 |
| Polyvinyl pyrrolidone | 1.70 |
| Colloidal silicon dioxide | 0.24 |
| Iron oxide yellow | 0.10 |
| Magnesium stearate | 0.49 |
| Controlled-Release Portion | |
| Doxycycline hyclate equivalent to doxycycline base 10 mg | 3.99 |
| Microcrystalline cellulose (Avicel ® PH-102) | 13.91 |
| Microcrystalline cellulose (Avicel ® PH-200) | 13.86 |
| Hydroxypropylmethyl cellulose (Methocel ® K100 LVCR) | 7.28 |
| Hydroxypropylmethyl cellulose (Methocel ® K4M CR) | 7.28 |
| Polyvinyl pyrrolidone | 1.46 |
| Colloidal silicon dioxide | 0.24 |
| Magnesium stearate | 0.48 |
| Coating | |
| Opadry ® | 3.00 |

Manufacturing Process
Immediate-Release Portion
1. Doxycycline hyclate, microcrystalline cellulose, crospovidone, polyvinyl pyrrolidone, colloidal silicon dioxide, magnesium stearate, and iron oxide yellow were mixed to form a blend.

Controlled-Release Portion
2. Doxycycline hyclate, microcrystalline cellulose, hydroxypropylmethyl cellulose, polyvinyl pyrrolidone, colloidal silicon dioxide, and magnesium stearate were mixed to form a blend.

Compression
3. The blend obtained in step 2 was compressed, followed by compression of the blend obtained in step 1 to form a bilayer tablet.
4. The bilayer tablet obtained in step 3 was further film-coated using Opadry®.

Example 9

| Ingredients | Quantity (% w/w) |
|---|---|
| Immediate-Release Portion | |
| Doxycycline monohydrate | 12.01 |
| Microcrystalline cellulose (Avicel ® PH-102) | 32.96 |
| Crospovidone | 4.31 |
| Colloidal silicon dioxide | 0.38 |
| Magnesium stearate | 0.35 |
| Controlled-Release Portion | |
| Doxycycline monohydrate | 4.00 |
| Microcrystalline cellulose (Avicel ® PH-102) | 14.51 |
| Lactose monohydrate | 14.52 |
| Hydroxypropylmethyl cellulose (Methocel ® K100 LVCR) | 8.08 |
| Hydroxypropylmethyl cellulose (Methocel ® K4M CR) | 8.08 |
| Colloidal silicon dioxide | 0.43 |
| Magnesium stearate | 0.38 |

Manufacturing Process
Immediate-Release Portion
1. Doxycycline monohydrate, microcrystalline cellulose, and colloidal silicon dioxide were mixed to form a blend.
2. Crospovidone was added to the blend obtained in step 1.
3. The blend obtained in step 2 was lubricated with magnesium stearate to form a final blend.

Controlled-Release Portion
4. Doxycycline monohydrate, microcrystalline cellulose, and colloidal silicon dioxide were mixed to form a blend.
5. Lactose monohydrate and hydroxypropylmethyl cellulose were added to the blend of step 4 and mixed to obtain a blend.
6. The blend obtained in step 5 was lubricated with magnesium stearate to form a final blend.

Compression
7. The final blend obtained in step 3 was compressed followed, by compression of the final blend obtained in step 6 to form a bilayer tablet.

Example 10

| Ingredients | Quantity (% w/w) |
|---|---|
| Immediate-Release Portion | |
| Doxycycline monohydrate | 12.01 |
| Microcrystalline cellulose (Avicel ® PH-102) | 32.96 |
| Crospovidone | 4.31 |
| Colloidal silicon dioxide | 0.38 |
| Magnesium stearate | 0.35 |
| Controlled-Release Portion | |
| Doxycycline monohydrate | 4.00 |
| Microcrystalline cellulose (Avicel ® PH-102) | 14.51 |
| Lactose monohydrate | 14.52 |
| Hydroxypropylmethyl cellulose (Methocel ® K4 MCR) | 16.15 |
| Colloidal silicon dioxide | 0.43 |
| Magnesium stearate | 0.38 |

Manufacturing Process
Immediate-Release Portion
1. Doxycycline monohydrate, microcrystalline cellulose, and colloidal silicon dioxide were mixed to form a blend.
2. Crospovidone was added to the blend obtained in step 1.
3. The blend obtained in step 2 was lubricated with magnesium stearate to form a final blend.

Controlled-Release Portion
4. Doxycycline monohydrate, microcrystalline cellulose, and colloidal silicon dioxide were mixed to form a blend.
5. Lactose monohydrate and hydroxypropylmethyl cellulose were added to the blend of step 4 and mixed to obtain a blend.
6. The blend obtained in step 5 was lubricated with magnesium stearate to form a final blend.

Compression
7. The final blend obtained in step 3 was compressed, followed by compression of the final blend obtained in step 6 to form a bilayer tablet.

Example 11

| Ingredients | Quantity (% w/w) |
|---|---|
| Immediate-Release Portion | |
| Doxycycline monohydrate | 10.41 |
| Microcrystalline cellulose (Avicel ® PH-102) | 34.56 |
| Crospovidone | 4.31 |
| Colloidal silicon dioxide | 0.38 |
| Magnesium stearate | 0.35 |
| Controlled-Release Portion | |
| Doxycycline monohydrate | 5.60 |
| Microcrystalline cellulose (Avicel ® PH-102) | 14.06 |
| Lactose monohydrate | 14.13 |
| Hydroxypropylmethyl cellulose (Methocel ® K100 LVCR) | 7.69 |
| Hydroxypropylmethyl cellulose (Methocel ® K4 MCR) | 7.69 |
| Colloidal silicon dioxide | 0.43 |
| Magnesium stearate | 0.38 |

Manufacturing Process
Immediate-Release Portion
1. Doxycycline monohydrate, microcrystalline cellulose, and colloidal silicon dioxide were mixed to form a blend.
2. Crospovidone was added to the blend obtained in step 1.
3. The blend obtained in step 2 was lubricated with magnesium stearate to form a final blend.

Controlled-Release Portion
4. Doxycycline monohydrate, microcrystalline cellulose, and colloidal silicon dioxide were mixed to form a blend.
5. Lactose monohydrate and hydroxypropylmethyl cellulose were added to the blend of step 4 and mixed to obtain a blend.
6. The blend obtained in step 5 was lubricated with magnesium stearate to form a final blend.

Compression
7. The final blend obtained in step 3 was compressed, followed by compression of the final blend obtained in step 6 to form a bilayer tablet.

Example 12

| Ingredients | Quantity (% w/w) |
|---|---|
| Immediate-Release Portion | |
| Doxycycline monohydrate | 10.40 |
| Microcrystalline cellulose (Avicel ® PH-102) | 34.50 |
| Crospovidone | 4.30 |
| Colloidal silicon dioxide | 0.40 |
| Magnesium stearate | 0.40 |
| Iron oxide yellow | 0.10 |
| Controlled-Release Portion | |
| Doxycycline monohydrate | 5.60 |
| Microcrystalline cellulose (Avicel ® PH-102) | 14.40 |
| Lactose monohydrate | 13.80 |
| Hydroxypropylmethyl cellulose (Methocel ® K4M CR) | 15.40 |
| Colloidal silicon dioxide | 0.40 |
| Magnesium stearate | 0.40 |
| Coating | |
| Opadry ® | 3.00 |

Manufacturing Process
Immediate-Release Portion
1. Doxycycline monohydrate, microcrystalline cellulose, iron oxide yellow, colloidal silicon dioxide, crospovidone, and magnesium stearate were mixed to form a blend.

Controlled-Release Portion
2. Doxycycline monohydrate, microcrystalline cellulose, and colloidal silicon dioxide were mixed to form a blend.
3. Lactose monohydrate and hydroxypropylmethyl cellulose were added to the blend of step 2 and mixed to obtain a blend.
4. The blend obtained in step 3 was lubricated with magnesium stearate to form a final blend.

Compression
5. The blend obtained in step 1 was compressed, followed by compression of the final blend obtained in step 4 to form a bilayer tablet.
6. The tablet obtained in step 5 was further film-coated using Opadry®.

Example 13

| Ingredients | Quantity (% w/w) |
|---|---|
| Immediate-Release Portion | |
| Doxycycline monohydrate | 9.61 |
| Microcrystalline cellulose (Avicel ® PH-102) | 35.25 |
| Crospovidone | 4.31 |
| Colloidal silicon dioxide | 0.38 |
| Magnesium stearate | 0.35 |
| Iron oxide yellow | 0.11 |
| Controlled-Release Portion | |
| Doxycycline monohydrate | 6.40 |
| Microcrystalline cellulose (Avicel ® PH-102) | 12.84 |
| Lactose monohydrate | 13.78 |

-continued

| Ingredients | Quantity (% w/w) |
|---|---|
| Hydroxypropylmethyl cellulose (Methocel ® K100 LVCR) | 8.08 |
| Hydroxypropylmethyl cellulose (Methocel ® K4M CR) | 8.08 |
| Colloidal silicon dioxide | 0.43 |
| Magnesium stearate | 0.38 |
| Coating | |
| Opadry ® | 2.99 |

Manufacturing Process

Immediate-Release Portion

1. Doxycycline monohydrate, microcrystalline cellulose, iron oxide yellow, crospovidone, colloidal silicon dioxide, and magnesium stearate were mixed to form a blend.

Controlled-Release Portion

2. Doxycycline monohydrate, microcrystalline cellulose, and colloidal silicon dioxide were mixed to form a blend.

3. Lactose monohydrate was added to the blend obtained in step 2, followed by the addition of hydroxypropylmethyl cellulose to obtain a blend.
4. The blend obtained in step 3 was lubricated with magnesium stearate to form a final blend.

Compression

5. The blend obtained in step 1 was compressed, followed by compression of the final blend obtained in step 4 to form a bilayer tablet.
6. The tablet obtained in step 5 was further film-coated using Opadry®.

Example 14

| Ingredients | Quantity (% w/w) |
|---|---|
| Doxycycline hyclate equivalent to doxycycline base 34 mg | 28.08 |
| Microcrystalline cellulose (Avicel ® PH-102) | 60.77 |

-continued

| Ingredients | Quantity (% w/w) |
|---|---|
| Crospovidone | 6.00 |
| Polyvinyl pyrrolidone | 3.50 |
| Colloidal silicon dioxide | 0.50 |
| Iron oxide yellow | 0.20 |
| Magnesium stearate | 1.00 |

Manufacturing Process

1. Doxycycline hyclate, Avicel® PH-102, iron oxide yellow, crospovidone, polyvinyl pyrrolidone, colloidal silicon dioxide, and magnesium stearate were mixed to form a blend.
2. The blend of step 1 was compressed into a tablet.

Bioavailability Studies

A bioavailability study was carried out to compare the doxycycline pharmaceutical composition prepared as per Example 1 of the present invention with Oracea® 40 mg capsules in healthy subjects under fasted and fed states. Table 1 provides the results of this study.

TABLE 1

Results of Bioavailability Study under Fasted and Fed States

| Parameter | Oracea ® fasted state ($R_{fasted}$) | Example 1 fasted state ($T_{fasted}$) | Example 1 fed state ($T_{fed}$) | $T_{fasted}/T_{fed}$ | $T_{fasted}/R_{fasted}$ | $(T_{fasted} - T_{fed}/T_{fasted})*100$ |
|---|---|---|---|---|---|---|
| $C_{max}$ | 311 | 265 | 214 | 1.24 | 0.85 | 19% |
| $AUC_{0-t}$ | 6313 | 4844 | 5212 | 0.93 | 0.77 | (~-7%) |

The data in Table 1 demonstrates that the pharmaceutical composition prepared as per the present invention has a reduced food effect wherein $C_{max}$ decreases by 19% and $AUC_{0-t}$ is almost unchanged (~-7%), as compared to the reference product Oracea® which shows decreases in $C_{max}$ and $AUC_{0-t}$ by 45% and 22%, respectively, when taken along with food.

Another bioavailability study was carried out to compare the doxycycline pharmaceutical composition prepared as per Example 2 of the present invention with Oracea® 40 mg capsules in healthy subjects under fasted and fed states. Table 2 provides the results of this study.

TABLE 2

Results of Bioavailability Study under Fasted and Fed States

| Parameter | Oracea ® fasted state ($R_{fasted}$) | Example 2 fasted state ($T_{fasted}$) | Example 2 fed state ($T_{fed}$) | $T_{fed}/T_{fasted}*$ | $T_{fasted}/R_{fasted}*$ | $(T_{fasted} - T_{fed}/T_{fasted})*100$ |
|---|---|---|---|---|---|---|
| $C_{max}$ | 391 | 397 | 290 | 76.32 | 97.23 | (~-27%) |
| $AUC_{0-t}$ | 6899 | 6522 | 6259 | 96.24 | 92.87 | (~-6%) |

*based on LSGM ratio

The data in Table 2 demonstrates that the pharmaceutical composition prepared as per the present invention has a reduced food effect wherein $C_{max}$ decreases by 27% and $AUC_{0-t}$ is almost unchanged (~-6%), as compared to the reference product Oracea® which shows decreases in $C_{max}$ and $AUC_{0-t}$ by 45% and 22%, respectively, when taken along with food.

Example 15

| Ingredients | Quantity (% w/w) |
|---|---|
| Doxycycline hyclate equivalent to doxycycline base 32 mg | 12.81 |
| Microcrystalline cellulose (Avicel ® PH-102) | 62.89 |
| Microcrystalline cellulose (Avicel ® PH-200) | 13.87 |
| Crospovidone | 2.91 |
| Polyvinyl pyrrolidone | 3.16 |
| Colloidal silicon dioxide | 0.49 |
| Magnesium stearate | 0.97 |
| Opadry ® | 2.91 |
| Purified water | q.s. |

Manufacturing Process
1. Doxycycline hyclate, crospovidone, polyvinyl pyrrolidone, and microcrystalline cellulose were blended.
2. The blend of step 1 was lubricated with colloidal silicon dioxide and magnesium stearate.
3. The lubricated blend of step 2 was compressed into tablets.
4. The tablets of step 3 were coated with Opadry®.

Example 16

| Ingredients | Quantity (% w/w) |
|---|---|
| Doxycycline hyclate equivalent to doxycycline base 32 mg | 12.81 |
| Microcrystalline cellulose (Avicel ® PH-102) | 53.18 |
| Microcrystalline cellulose (Avicel ® PH-200) | 13.87 |
| Crospovidone | 2.91 |
| Polyvinyl pyrrolidone | 3.16 |
| Hydroxypropylmethyl cellulose (Methocel ® K4 MCR) | 2.43 |
| Hydroxypropylmethyl cellulose (Methocel ® K100 premium LVCR) | 7.28 |
| Colloidal silicon dioxide | 0.49 |
| Magnesium stearate | 0.97 |
| Opadry ® | 2.91 |
| Purified water | q.s. |

Manufacturing Process
1. Doxycycline hyclate, crospovidone, polyvinyl pyrrolidone, microcrystalline cellulose, and hydroxypropylmethyl cellulose were blended.
2. The blend of step 1 was lubricated with colloidal silicon dioxide and magnesium stearate.
3. The lubricated blend of step 2 was compressed into tablets.
4. The tablets of step 3 were coated with Opadry®.

Example 17

| Ingredients | Quantity (% w/w) |
|---|---|
| Doxycycline hyclate equivalent to doxycycline base 36 mg | 14.41 |
| Microcrystalline cellulose (Avicel ®-PH102) | 61.29 |
| Microcrystalline cellulose (Avicel ®-PH 200) | 13.87 |
| Crospovidone | 2.91 |
| Polyvinyl pyrrolidone | 3.16 |
| Colloidal silicon dioxide | 0.49 |
| Magnesium stearate | 0.97 |
| Opadry ® | 2.91 |
| Purified water | q.s. |

Manufacturing Process
1. Doxycycline hyclate, crospovidone, polyvinyl pyrrolidone, and microcrystalline cellulose were blended.
2. The blend of step 1 was lubricated with colloidal silicon dioxide and magnesium stearate.
3. The lubricated blend of step 2 was compressed into tablets.
4. The tablets of step 3 were coated with Opadry®.

Example 18

| Ingredients | Quantity (% w/w) |
|---|---|
| Doxycycline hyclate equivalent to doxycycline base 36 mg | 14.41 |
| Microcrystalline cellulose (Avicel ® PH-102) | 51.58 |
| Microcrystalline cellulose (Avicel ® PH-200) | 13.87 |
| Crospovidone | 2.91 |
| Polyvinyl pyrrolidone | 3.16 |
| Hydroxypropylmethyl cellulose (Methocel ® K4 MCR) | 2.43 |
| Hydroxypropylmethyl cellulose (Methocel ® K100 premium LVCR) | 7.28 |
| Colloidal silicon dioxide | 0.49 |
| Magnesium stearate | 0.97 |
| Opadry ® | 2.91 |
| Purified water | q.s. |

Manufacturing Process
1. Doxycycline hyclate, crospovidone, polyvinyl pyrrolidone, microcrystalline cellulose, and hydroxypropylmethyl cellulose were blended.
2. The blended material of step 1 was lubricated with colloidal silicon dioxide and magnesium stearate.
3. The lubricated blend of step 2 was compressed into tablets.
4. The tablets of step 3 were coated with Opadry®.

Example 19

| Ingredients | Quantity (% w/w) |
|---|---|
| Doxycycline hyclate equivalent to doxycycline base 36 mg | 14.41 |
| Microcrystalline cellulose (Avicel ® PH-102) | 46.72 |
| Microcrystalline cellulose (Avicel ® PH-200) | 13.87 |
| Crospovidone | 2.91 |
| Polyvinyl pyrrolidone | 3.16 |
| Hydroxypropylmethyl cellulose (Methocel ® K4 MCR) | 7.28 |
| Hydroxypropylmethyl cellulose (Methocel ® K100 premium LVCR) | 7.28 |
| Colloidal silicon dioxide | 0.49 |
| Magnesium stearate | 0.97 |
| Coating | |
| Opadry ® | 2.91 |
| Purified water | q.s. |

Manufacturing Process
1. Doxycycline hyclate, crospovidone, microcrystalline cellulose, hydroxypropylmethyl cellulose, and polyvinyl pyrrolidone were blended.
2. The blended material of step 1 was lubricated with colloidal silicon dioxide and magnesium stearate.
3. The lubricated blend of step 2 was compressed into tablets.
4. The tablets of step 3 were coated with Opadry®.

Example 20

| Ingredients | Quantity (% w/w) |
|---|---|
| Doxycycline hyclate equivalent to doxycycline base 36 mg | 14.41 |
| Microcrystalline cellulose (Avicel ® PH-102) | 49.15 |
| Microcrystalline cellulose (Avicel ® PH-200) | 13.87 |
| Crospovidone | 2.91 |
| Polyvinyl pyrrolidone | 3.16 |
| Hydroxypropylmethyl cellulose (Methocel ® K100 premium LVCR) | 12.14 |
| Colloidal silicon dioxide | 0.49 |
| Magnesium stearate | 0.97 |
| Opadry ® | 2.91 |
| Purified water | q.s. |

Manufacturing Process
1. Doxycycline hyclate, crospovidone, polyvinyl pyrrolidone, microcrystalline cellulose, and hydroxypropylmethyl cellulose were blended.
2. The blended material of step 1 was lubricated with colloidal silicon dioxide and magnesium stearate.
3. The lubricated blend of step 2 was compressed into tablets.
4. The tablets of step 3 were coated with Opadry®.

Example 21

| Ingredients | Quantity (% w/w) |
|---|---|
| Immediate-Release Layer | |
| Doxycycline hyclate equivalent to doxycycline base 30.0 mg | 12.01 |
| Microcrystalline cellulose (Avicel ® PH-102) | 31.10 |
| Crospovidone | 2.91 |
| Polyvinyl pyrrolidone | 1.70 |
| Iron oxide yellow | 0.10 |
| Colloidal silicon dioxide | 0.24 |
| Magnesium stearate | 0.49 |
| Controlled-Release Layer | |
| Doxycycline hyclate equivalent to doxycycline 6.0 mg | 2.40 |
| Microcrystalline cellulose (Avicel ® PH-102) | 15.53 |
| Microcrystalline cellulose (Avicel ® PH-200) | 13.87 |
| Hydroxypropylmethyl cellulose (Methocel ® K100 premium LVCR) | 14.56 |
| Polyvinyl pyrrolidone | 1.46 |
| Colloidal silicon dioxide | 0.24 |
| Magnesium stearate | 0.49 |
| Opadry ® | 2.91 |
| Purified water | q.s. |

Manufacturing Process
Immediate-Release Layer
1. Doxycycline hyclate, polyvinyl pyrrolidone, crospovidone, microcrystalline cellulose, and iron oxide yellow were blended.
2. The blend of step 1 was lubricated with colloidal silicon dioxide and magnesium stearate.
Controlled-Release Layer
3. Doxycycline hyclate, hydroxypropylmethyl cellulose, polyvinyl pyrrolidone, and microcrystalline cellulose were blended.
4. The blend of step 3 was lubricated with colloidal silicon dioxide and magnesium stearate.
Compression
5. The lubricated blends of step 2 and step 4 were compressed to give bilayer tablets.
6. The tablets of step 5 were coated with Opadry®.

Example 22

| Ingredients | Quantity (% w/w) |
|---|---|
| Doxycycline hyclate equivalent to doxycycline base 36 mg | 14.41 |
| Microcrystalline cellulose (Avicel ® PH-102) | 43.95 |
| Microcrystalline cellulose (Avicel ® PH-200) | 13.86 |
| Tartaric acid pellets | 5.20 |
| Crospovidone | 2.91 |
| Polyvinyl pyrrolidone | 3.16 |
| Hydroxypropylmethyl cellulose (Methocel ® K100 premium LVCR) | 12.14 |
| Colloidal silicon dioxide | 0.49 |
| Magnesium stearate | 0.97 |
| Opadry ® | 2.91 |
| Purified water | q.s. |

Manufacturing Process
1. Doxycycline hyclate, crospovidone, microcrystalline cellulose, hydroxypropylmethyl cellulose, polyvinyl pyrrolidone, and tartaric acid were blended.
2. The blended material of step 1 was lubricated with colloidal silicon dioxide and magnesium stearate.
3. The lubricated blend of step 2 was compressed into tablets.
4. The tablets of step 3 were coated with Opadry®.

Example 23

| Ingredients | Quantity (% w/w) |
|---|---|
| Doxycycline hyclate equivalent to doxycycline base 32 mg | 12.81 |
| Microcrystalline cellulose (Avicel ® PH-102) | 45.55 |
| Microcrystalline cellulose (Avicel ® PH-200) | 13.87 |
| Tartaric acid pellets | 5.20 |
| Crospovidone | 2.91 |
| Polyvinyl pyrrolidone | 3.16 |
| Hydroxypropylmethyl cellulose (Methocel ® K100 premium LVCR) | 12.14 |
| Colloidal silicon dioxide | 0.49 |
| Magnesium stearate | 0.97 |
| Opadry ® | 2.91 |
| Purified water | q.s. |

Manufacturing Process
1. Doxycycline hyclate, crospovidone, microcrystalline cellulose, hydroxypropylmethyl cellulose, polyvinyl pyrrolidone, and tartaric acid were blended.
2. The blended material of step 1 was lubricated with colloidal silicon dioxide and magnesium stearate.
3. The lubricated blend of step 2 was compressed into tablets.
4. The tablets of step 3 were coated with Opadry®.

Example 24

| Ingredients | Quantity (% w/w) |
|---|---|
| Doxycycline hyclate equivalent to doxycycline 32 mg | 18.47 |
| Hydroxypropylmethyl cellulose | 1.54 |

-continued

| Ingredients | Quantity (% w/w) |
|---|---|
| Sugar spheres | 80.00 |
| Purified water | q.s. |

Manufacturing Process:
1. Hydroxypropylmethyl cellulose is dissolved in purified water to form a binder solution.
2. Doxycycline is added to the binder solution of step 1 to form a drug-binder solution.
3. Sugar spheres are coated with the drug-binder solution of step 2 to obtain coated pellets.
4. The coated pellets of step 3 are dried, then filled into capsules.

Example 25

| Ingredients | Quantity (% w/w) |
|---|---|
| Doxycycline hyclate equivalent to doxycycline 34 mg | 19.62 |
| Hydroxypropylmethyl cellulose | 2.38 |
| Sugar spheres | 78.00 |
| Purified water | q.s. |

Manufacturing Process:
1. Hydroxypropylmethyl cellulose is dissolved in purified water to form a binder solution.
2. Doxycycline is added to the binder solution of step 1 to form a drug-binder solution.
3. Sugar spheres are coated with the drug-binder solution of step 2 to obtain coated pellets.
4. The coated pellets of step 3 are dried, then filled into capsules.

Example 26

| Ingredients | Quantity (% w/w) |
|---|---|
| Doxycycline monohydrate equivalent to doxycycline 32 mg | 17.69 |
| Hydroxypropylmethyl cellulose | 2.91 |
| Sugar spheres | 79.40 |
| Purified water | q.s. |

Manufacturing Process:
1. Hydroxypropylmethyl cellulose is dissolved in purified water to obtain a binder solution.
2. Doxycycline is added to the binder solution of step 1 to form a drug-binder solution.
3. Sugar spheres are coated with the drug-binder solution of step 2 to obtain coated pellets.
4. The coated pellets of step 3 are dried, then filled into capsules.

We claim:

1. A once daily pharmaceutical composition comprising doxycycline, a controlled-release polymer, and one or more pharmaceutically acceptable excipients, wherein the pharmaceutical composition contains up to 40 mg of doxycycline.

2. The once daily pharmaceutical composition according to claim 1, wherein the pharmaceutical composition contains from 24 mg to 40 mg of doxycycline.

3. The once daily pharmaceutical composition according to claim 1, wherein the pharmaceutical composition contains 40 mg of doxycycline.

4. The once daily pharmaceutical composition according to claim 1, wherein the pharmaceutical composition contains 36 mg of doxycycline.

5. The once daily pharmaceutical composition according to claim 1, wherein the pharmaceutical composition contains 32 mg of doxycycline.

6. The once daily pharmaceutical composition according to claim 1, wherein the pharmaceutical composition contains 30 mg of doxycycline.

7. The once daily pharmaceutical composition according to claim 1, wherein the doxycycline is present as a salt, hydrate, or a solvate.

8. The once daily pharmaceutical composition according to claim 7, wherein the doxycycline is present as doxycycline hyclate.

9. The once daily pharmaceutical composition according to claim 7, wherein the doxycycline is present as doxycycline monohydrate.

10. The once daily pharmaceutical composition according to claim 1, wherein the pharmaceutical composition is a capsule or a tablet.

11. The once daily pharmaceutical composition according to claim 1, wherein the pharmaceutical composition is in the form of pellets, beads, beadlets, granules, spheres or spheroids, minitablets, particles, or powders.

12. The once daily pharmaceutical composition according to claim 10, wherein the pharmaceutical composition is a capsule filled with one or more of pellets, beads, beadlets, granules, spheres or spheroids, minitablets, particles, or powders.

13. The once daily pharmaceutical composition according to claim 1, wherein the pharmaceutical composition exhibits a reduced food effect such that the food effect on $C_{max}$ is less than 40% and/or $AUC_{0-t}$ is less than 20% as compared to when the pharmaceutical composition is administered in a fasted state.

14. A method of treating rosacea by administering to a person in need thereof a once daily pharmaceutical composition comprising doxycycline, a controlled-release polymer, and one or more pharmaceutically acceptable excipients, wherein the pharmaceutical composition contains up to 40 mg of doxycycline.

* * * * *